United States Patent
Leung

(10) Patent No.: US 10,732,169 B2
(45) Date of Patent: Aug. 4, 2020

(54) PERSONALIZED HEALTHCARE P4 DRUG MONITORING SYSTEM AND METHOD

(71) Applicant: eNano Health Limited, Hong Kong SAR (HK)

(72) Inventor: Patrick Shau-park Leung, Arcadia, CA (US)

(*) Notice: Subject to any disclaimer, the term of this patent is extended or adjusted under 35 U.S.C. 154(b) by 0 days.

(21) Appl. No.: 16/374,798

(22) Filed: Apr. 4, 2019

(65) Prior Publication Data
US 2019/0219565 A1   Jul. 18, 2019

Related U.S. Application Data

(63) Continuation-in-part of application No. 15/469,138, filed on Mar. 24, 2017, now Pat. No. 10,513,725, and
(Continued)

(51) Int. Cl.
*G01N 33/50* (2006.01)
*G01N 33/68* (2006.01)
(Continued)

(52) U.S. Cl.
CPC ....... *G01N 33/5008* (2013.01); *A61B 5/1477* (2013.01); *A61B 10/0051* (2013.01);
(Continued)

(58) Field of Classification Search
CPC ............. G01N 33/5008; G01N 33/66; G01N 33/6848; G01N 2030/8836; G01N 30/72;
(Continued)

(56) References Cited

U.S. PATENT DOCUMENTS

| | | | |
|---|---|---|---|
| 2012/0164674 A1* | 6/2012 | Selinfreund | C12Q 1/28 435/22 |
| 2014/0235963 A1* | 8/2014 | Edwards | A61B 5/0022 600/301 |
| 2014/0296089 A1* | 10/2014 | Holmes | G01N 35/026 506/9 |

OTHER PUBLICATIONS

"A DIY medical diagnosis app" Mar. 23, 2014, weblink: https://www.kurzweilai.net/a-diy-medical-diagnosis-app accessed on Dec. 19, 2019, pp. 1-3 (Year: 2014).*

* cited by examiner

*Primary Examiner* — Dennis White
(74) *Attorney, Agent, or Firm* — James C. Schroeder; Bioinnovation Legal PLLC

(57) ABSTRACT

The claimed invention provides real-time and subsequent analysis personalized user based health, wellness and pharmaceutical and illicit drug detection information. Non-invasive techniques utilize saliva for body levels of wellness indicators and pharmaceutical and illicit drug ingestion which are coordinated over time. Saliva captured on sample strips are real-time indicator reviewed and subsequently analyzed using traditional analytical chemistry techniques including liquid chromatography/mass spectrometry (LC/MS) and coordinated with time of administration with optional genetic sequence analysis to confirm related disease conditions. By using P4 (Participatory, Personalized, Predictive, and Preventive) health management techniques the patient determines if the pharmaceutical is having the correct and desired effect for maximum therapeutic benefit. While illustrative embodiments detecting Metformin and Keppra are provided the system has broad pharmaceutical and illicit drug monitoring applicability.

6 Claims, 16 Drawing Sheets
Specification includes a Sequence Listing.

An illustrated diagram of KT3 & P4 combo test

Related U.S. Application Data a continuation-in-part of application No. 15/056,163, filed on Feb. 29, 2016, now Pat. No. 10,506,954.

(60) Provisional application No. 62/653,543, filed on Apr. 5, 2018.

(51) Int. Cl.
| | |
|---|---|
| *C12Q 1/28* | (2006.01) |
| *G01N 33/66* | (2006.01) |
| *A61B 10/00* | (2006.01) |
| *C12Q 1/54* | (2006.01) |
| *A61B 5/1477* | (2006.01) |
| *G01N 33/487* | (2006.01) |
| *A61B 5/145* | (2006.01) |
| *G01N 30/72* | (2006.01) |
| *G01N 30/88* | (2006.01) |

(52) U.S. Cl.
CPC ............... *C12Q 1/28* (2013.01); *C12Q 1/54* (2013.01); *G01N 33/66* (2013.01); *G01N 33/6848* (2013.01); *A61B 5/14532* (2013.01); *A61B 2010/0006* (2013.01); *A61B 2010/0009* (2013.01); *G01N 30/72* (2013.01); *G01N 33/48792* (2013.01); *G01N 2030/8836* (2013.01); *G01N 2333/62* (2013.01); *G01N 2800/52* (2013.01)

(58) Field of Classification Search
CPC ......... G01N 33/48792; G01N 2800/52; G01N 2333/62; C12Q 1/54; C12Q 1/28; A61B 5/1477; A61B 10/0051; A61B 2010/0006; A61B 2010/0009; A61B 5/14532

See application file for complete search history.

*An illustrated diagram of KT3 & P4 combo test*

1701

PERSONALIZED HEALTHCARE P4 DRUG MONITORING SYSTEM AND METHOD

CITATION LIST

Patent Literature

This patent application claims priority to provisional patent application 62/653,543 filed Apr. 5, 2018. This patent application is additionally a continuation-in-part and claims priority to U.S. patent application Ser. No. 15/666,699 filed Aug. 2, 2017 to Patrick Shau-park Leung entitled "Personalized Glucose and Insulin Monitoring System." In addition, this patent application is a continuation-in-part and claims priority to U.S. patent application Ser. No. 15/469,138 filed Mar. 24, 2017 to Patrick Shau-park Leung entitled "Public personalized mobile health sensing system, method and device" which is a continuation of U.S. patent application Ser. No. 15/056,163 filed Feb. 29, 2016 to Patrick Shau-park Leung entitled "Mobile automated health sensing system, method and device".

TECHNICAL FIELD

The claimed invention relates to real-time biomedical healthcare patient monitoring based upon the P4 (Participatory, Personalized, Predictive, and Preventive) health management method. With greater particularity, the claimed invention addresses personalized monitoring of prescription pharmaceuticals as well as illicit drugs using saliva with patient alerting and artificial intelligence data interpretation.

BACKGROUND ART

Traditional biomedical monitoring of patient pharmaceutical administration is often clinical in nature with results ordered by a doctor in a hospital or medical office setting and performed in a centralized laboratory setting. Even when patients are informed as to the blood levels of their pharmaceutical body chemistry it is often through the lens of the primary medical provider.

Using traditional methods, if a patient wishes to know detailed information about personal pharmaceutical levels in the body they must first schedule an office visit. Absent an emergency, such visits usually take place weeks to months after the request is made. To determine body levels of pharmaceutical products ingested, blood is drawn and sent to an outside laboratory. Several days later the results are reported back to the primary healthcare physician who interprets the laboratory results and provides a high level summary to the patient.

Despite the rapid expansion of 'big data' healthcare information, patients are rarely the owners or curators of their own healthcare information leading to reduced choices and far fewer options in healthcare data portability when seeking out alternate providers.

SUMMARY OF INVENTION

Technical Problem

Current systems for monitoring of prescription pharmaceutical levels in the human body are centralized and exclusionary. They are not participatory apart from the blood sample that the patient provides for testing. Reporting of pharmaceutical levels are not personalized in that apart from the unique data itself released by a medical healthcare provider, the medical service provider controls the manner, method and timing of information content release. The technical problems of pharmaceutical level monitoring are primarily systematic in nature due to legal and healthcare provider process constraints around the information itself.

Apart from information distribution restrictions, drawing of patient blood in a clinical setting creates a number of challenges including sample perishability, hazardous waste disposal and personal bias against invasive procedures. Traditional laboratory nitrocellulose paper is often unsuitable for sample collection conjugated with analytical reporting chemicals.

Solution to Problem

The claimed invention utilizes saliva for small-molecule drug detection.

Saliva is used a diagnostic tool for therapeutic drug monitoring, as lateral flow sample captured saliva samples can accurately reflect drug level in the body at different time points. The claimed invention highlights the use of saliva as a diagnostic tool for measuring medication adherence by detecting the presence of small-molecule drugs in saliva. As a direct and intended consequence, the claimed invention is able to determine whether a patient is taking prescribed (and proscribed) medications with optional reminders sent to patients if the patient had forgotten to take prescribed medicine. By embracing the P4 (Participatory, Personalized, Predictive, and Preventive) health management method, the claimed invention provides patient engaging pharmaceutical administration information. By utilizing patient saliva samples which are locally analyzed then transported to a centralized analysis facility, pharmaceutical and pharmaceutical carrier information is accurately captured and rapidly delivered to the patient using a smartphone or personal computing device.

Patient pharmaceutical and pharmaceutical carrier level information is non-invasively obtained by saliva samples collected on disposable sample means including lateral flow sample strips. Local analysis is complemented by using traditional laboratory equipment including Liquid Chromatography/Mass Spectrometry (LC/MS), pharmaceutical and carrier levels are obtained and reported back to the patient directly using secure internet data transmission techniques. Enhancements to salivary sample capture in combination with analytical reporting chemicals include optimized lateral flow strip material.

Advantageous Effects of Invention

By empowering the patient to cultivate their own pharmaceutical body level information, predictive and preventative wellness is enabled. The claimed invention is distinguishable from using traditional blood level monitoring due to the powerful wellness knowledge enabled by calculating time of pharmaceutical administration against the results obtained by the saliva/lateral flow sample strip conjugate analyzed by LC/MS.

In a doctor's office, the drawn blood sample reflects a single point of time measured infrequently separated by months or years. In the claimed invention, the time of pharmaceutical administration as well as the time of sample collection is known. With regular patient monitoring it is an expected and intended consequence that over-administration of pharmaceutical products (by patients forgetting if they had taken their medication and inadvertently readministering it) as well as omitting pharmaceutical administration will be detectable and reportable to the patient and relevant family members and health care providers.

In addition, patient privacy is maintained as no patient identifiable information needs to be included in the collection device when it is independently analyzed.

BRIEF DESCRIPTION OF DRAWINGS

The accompanying drawings are included to better illustrate exemplary embodiments of the claimed invention.

DESCRIPTION OF EMBODIMENTS

P4 Medicine is Predictive, Preventive, Personalized and Participatory. Its two major objectives are to quantify wellness and demystify disease. In the illustrative examples contained herein, the aims of P4 Medicine are achieved by combining end-user analysis of current health metrics together with follow-on lab analytics of the same saliva sample to determine body levels of administered pharmaceuticals. In a first illustrative example, user health data is gathered by smartphone to capture pharmaceutical administration and related health details such as time food intake.

Optionally, the system may be combined with glucose measuring test strips to report glucose levels to the end-user for personalized and participatory wellness monitoring. The same test strip subsequently analyzed using standard analytical equipment, however, provides the opportunity for predictive and preventative health screening based upon detection of pharmaceuticals and their carriers as well as DNA, RNA and protein indicators of body health as well as the presence or absence of harmful bacteria, viruses and other disease carriers.

EXAMPLES

The optimal management of health using correct pharmaceutical dosing and timing of administration is best managed by the patient. Unfortunately, patients rarely have access to the clinical tools needed for optimal pharmaceutical administration. The first illustrative example depicts the administration of the drug metformin so that using the claimed invention the patient can match drug dosing so that it is optimal for food intake. While metformin is utilized as an illustrative example the claimed invention is not intended to be limited to a particular pharmaceutical or disease state but instead intended for broad health management opportunities.

Examples

Example 1

Figure 1:
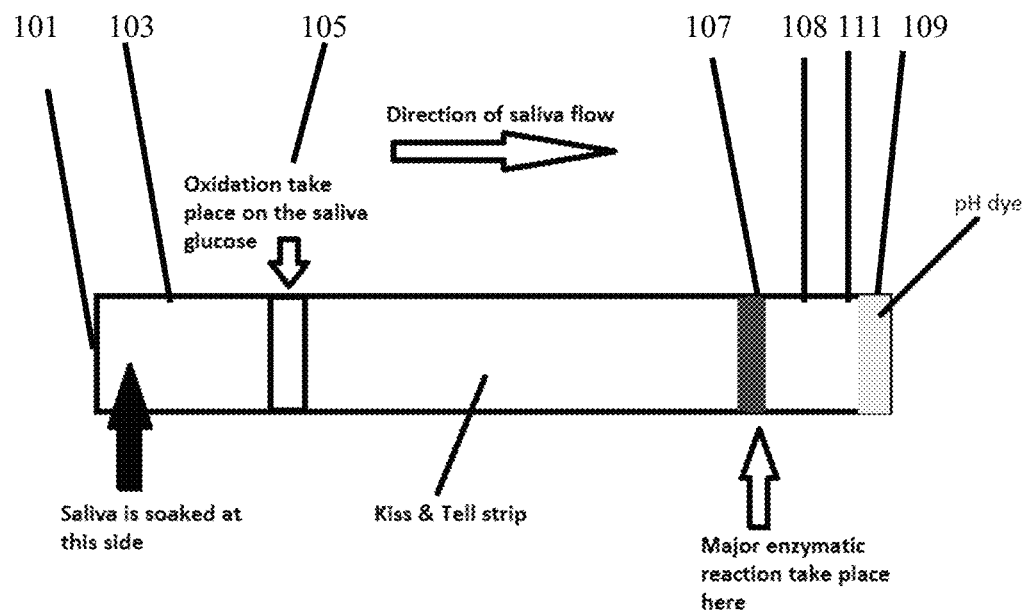
FIG. 1 is a top level schematic illustration of saliva derived drug level test strip with enhanced functionality.

The claimed P4 drug testing wellness platform is based upon salivary capture and analysis using one or more disposable test strips. FIG. 1 depicts salivary test strip (101) which captures saliva (not shown) at salivary capture area (103) which is distributed by lateral flow into oxidation region (105) and onto enzymatic region (107) concluding with optional pH region (109). In the first illustrative embodiment the local enzymatic analysis provides locally measurable salivary indicator levels and may additionally incorporate antibody indicator region (108) as well as optional aptamer indicator region (111).

In the first illustrative example, pharmaceutical levels are captured by placing test strip (101) in a user's mouth (not shown) for two minutes to distribute saliva (not shown) to test strip (101).

Adequate saliva capture is confirmed by illumination of pH region (109). In the first illustrative example, the user waits an additional three minutes upon which a measurable color change takes place at enzymatic region (107). Salivary indicator levels may be estimated by user color comparison visually or by computer analysis by a smartphone type device (not shown). The detection of salivary glucose is based on a coupling reaction between glucose oxidase and peroxidase. Glucose oxidase oxidizes the salivary glucose into gluconolactone and hydrogen peroxide (H2O2). In the presence of peroxidase, 10-acetyl-3,7-dihydroxyphenoxazine reacts with H2O2 in a 1:1 stoichiometry in order to produce a white to pink color. In a preferred embodiment, the chemical sensor at enzymatic region (107) is a compound having the following structural formula:

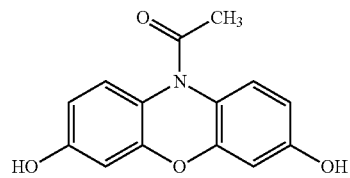 [SMILES: CC(=O)N1c2ccc(O)cc2Oc2cc(O)ccc21]

Figure 2:
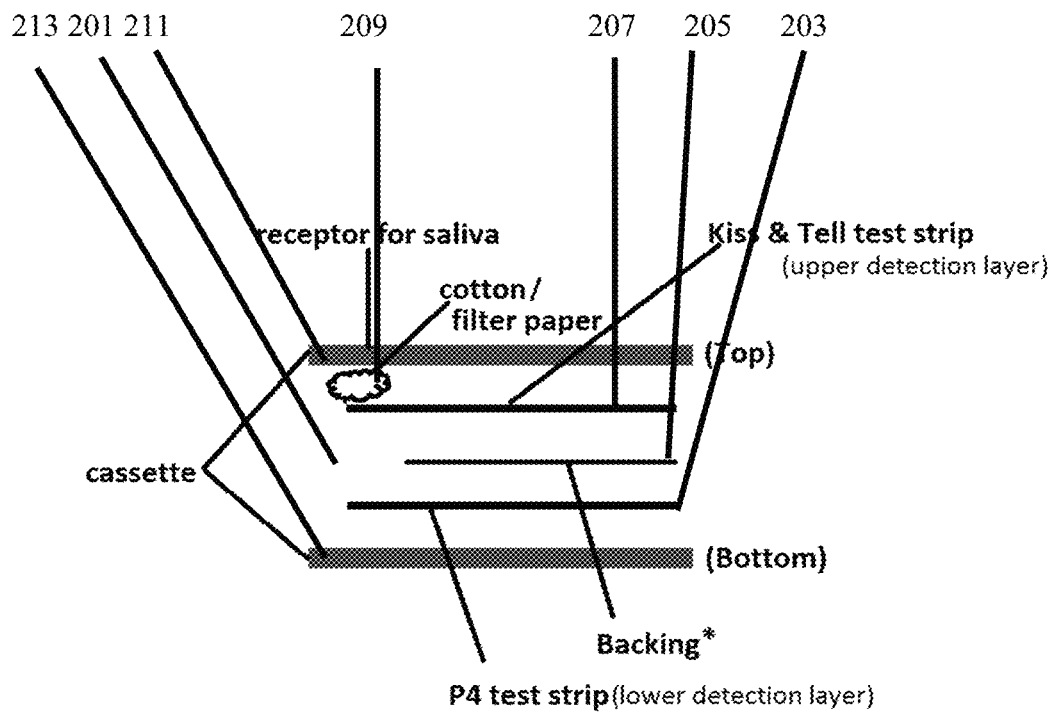
FIG. 2 is a side view schematic illustration of saliva derived drug level test strip with additional functionality.

In the first illustrative embodiment, the salivary test strip may be single purpose as illustrated by salivary test strip (101) depicted by FIG. 1 or multi-purpose as illustrated by multi-function salivary test strip (201) depicted in FIG. 2. FIG. 2 multi-function salivary test strip (201) is multi-layer with top analytical layer (207), layer divider (205) backing and lower analytical layer (203). Saliva access is provided through optional cassette housing (213) with salivary receptacle (211) which distributes saliva (not shown) through optional saliva wicking material (209) which can be cotton, filter paper or other material suitable for distribution of saliva. In a preferred embodiment, optimized analytical lateral flow material is utilized for top analytical layer (207) and/or lower analytical layer (203) which is distinguishable from traditional nitrocellulose filter paper by absorbency rate and internal composition. Distinguishable characteristics from traditional nitrocellulose paper include high hydrophilic behavior wicking 4 cm in under 50 seconds. Optimal analytical flow material characteristics include highly efficient body fluid separation with no analyte interference, excellent release with both latex and gold conjugates, reaction membrane to capture reagents bound to the immobilized latex beads combined with conjugate and analyte to give intense capture lines and superior sample wicking with no loss of assay sensitivity when compared to other materials and acting as an absorbent to liquids.

Both pharmaceutical and illicit drug levels are derived from the user's saliva. Saliva is unlike blood in that it is stable at room temperature for long periods of time, safe to collect and transport and not considered medical waste.

Example 2

Figure 3:
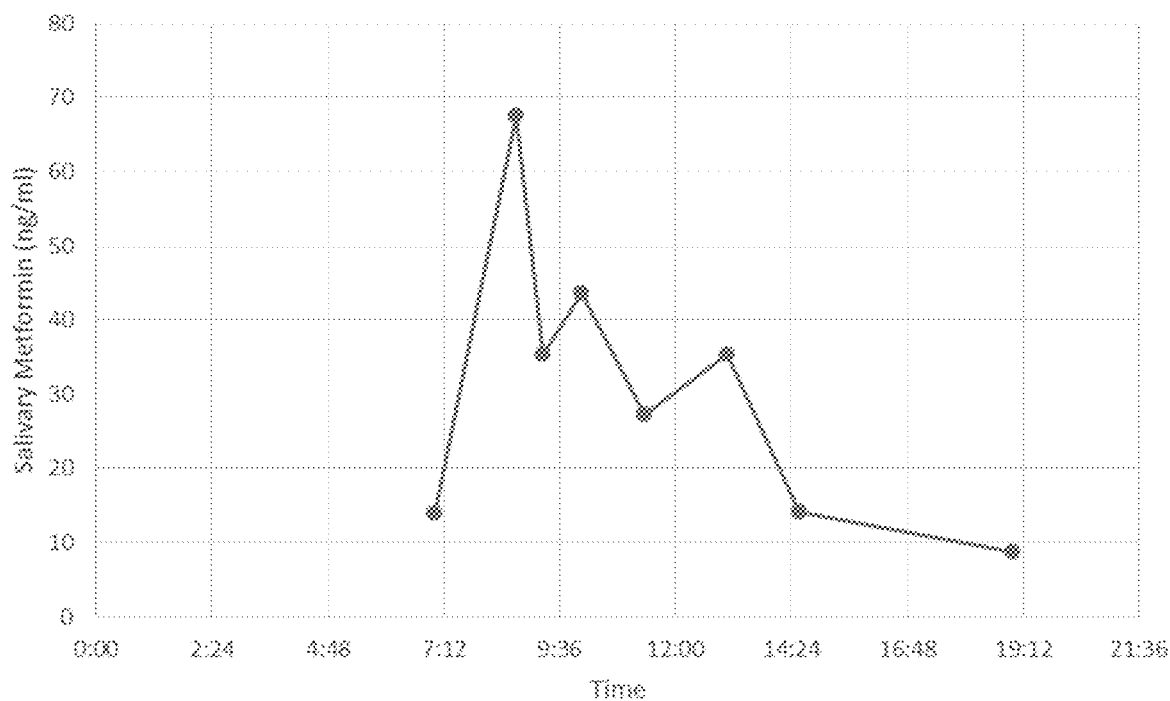
FIG. 3 is a graphical chart illustration of saliva derived pharmaceutical metformin levels over time.

Metformin (Metformin hydrochloride) is a type of medicine known as a biguanide. The drug works to lower the amount of sugar in the blood of people with diabetes. It does this by lowering the amount of sugar produced in the liver, and also increasing the sensitivity of muscle cells to insulin. FIG. 3 illustrates traditional metformin administration which results in imprecise and inefficient pharmaceutical administration owing to the absence of guidance from the claimed invention. In FIG. 3 the peak of metformin levels in the body do not correspond to the times of greatest need during major mealtimes.

Figure 4:
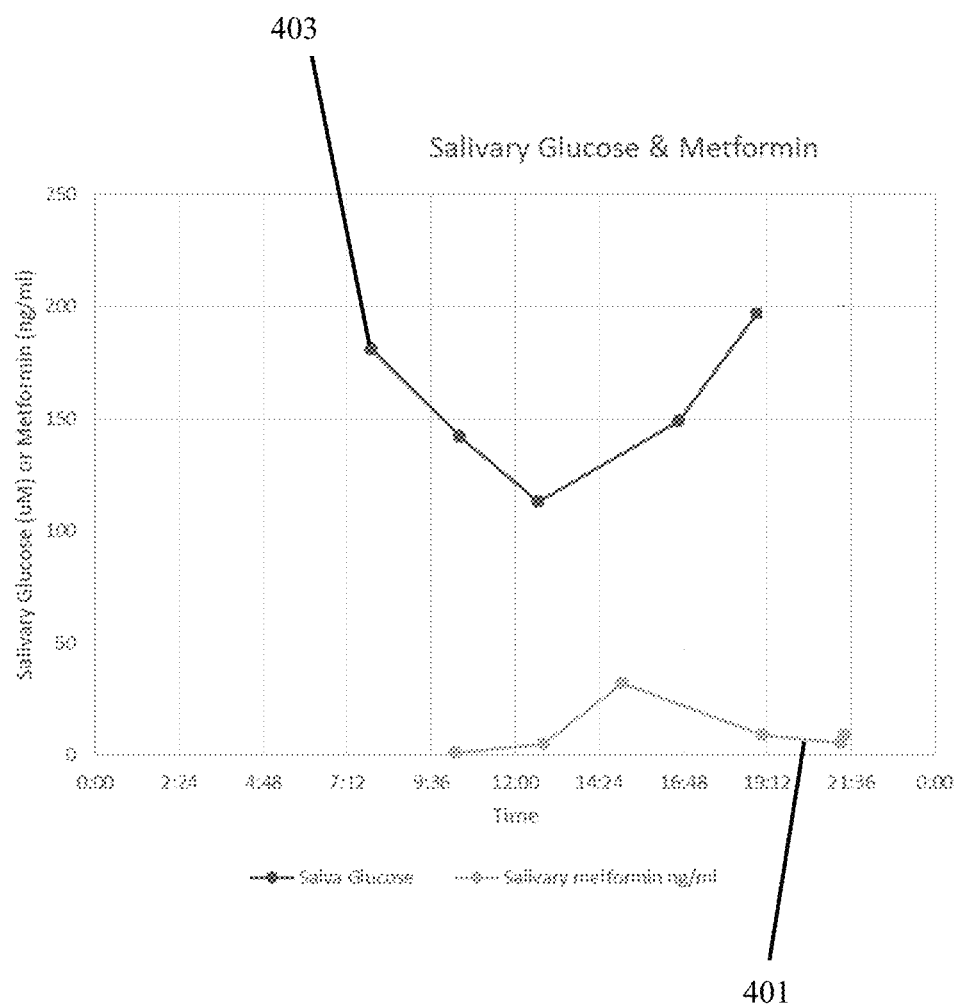
FIG. 4 is a graphical chart illustration of metformin drug and glucose levels over time.

FIG. 4 illustrates metformin levels (401) in the body depicted as a function of time and plotted against corresponding glucose levels (403). Administration of metformin traditionally utilizes a 'best guess' of when the drug will be at optimum therapeutic levels. In the illustrative Example 2 representative FIG. 4 the drug level to body condition graphical peaks are not aligned.

In preferred embodiment Example 2 detailed below a user captures glucose data in near real time utilizing a plurality of multi-function salivary test strips which are subsequently remotely analyzed for metformin. It is a direct and intended consequence of the claimed invention that measuring pharmaceutical levels and glucose from saliva provides more immediate and relevant composite wellness picture owing to the delay between meal ingestion and corresponding blood levels. In the second illustrative example the user is able to locally capture glucose information shortly after sample exposure.

To obtain pharmaceutical levels of metformin in the second illustrative example sample test strip (201) is mailed to a remote location for further analysis using traditional laboratory equipment such as LC/MS. Local analysis of glucose is by illustration only and not by limitation as any target capable of local enzymatic, aptamer and/or antibody analysis may be captured. By using a smartphone to input time of saliva sample data capture as well as most recent mealtime, glucose results are immediately captured and metformin results are subsequently returned to generate results allowing the user to determine general wellness indicators including ideal time for metformin pharmaceutical administration. A primary goal of this embodiment of the claimed invention is to allow the patient to best align the maximum therapeutic effect of metformin for processing of blood glucose after a meal is eaten by the patient.

Figure 5:
FIG. 5 is a graphical chart illustration of saliva derived body pharmaceutical content plotted by time.

FIG. 5 the drug level to body condition graphical peaks are enabled and optimized due to feedback from the claimed invention. Through active body salivary chemistry analysis and pharmaceutical administration tracking achieved through use of the claimed invention, the optimal dosing is achieved by aligning the peak pharmaceutical level (501) with lowest amount of salivary glucose (503).

Figure 6:
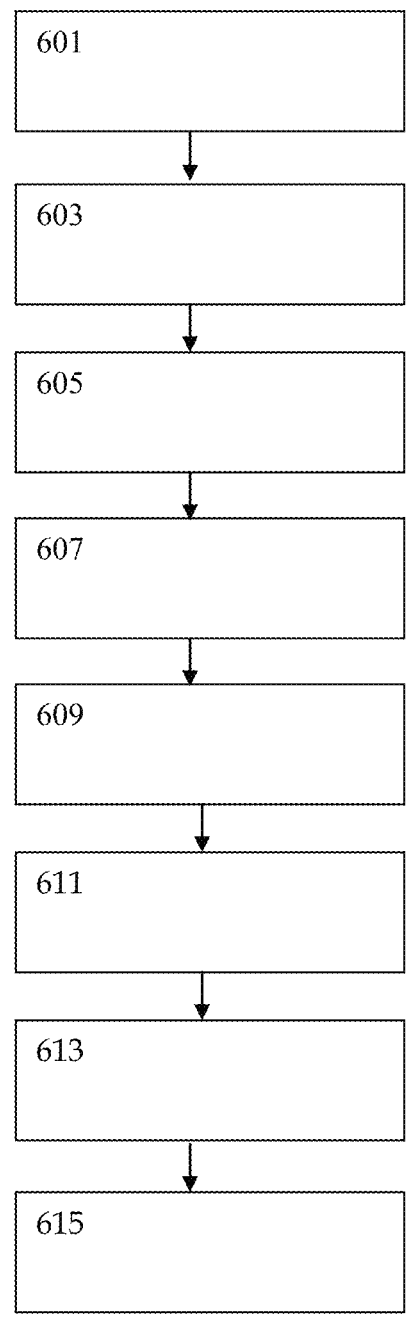
FIG. 6 is a flowchart illustrating a preferred embodiment of the claimed invention.

FIG. 6 illustrates the process of utilizing the claimed invention to manage the administration of metformin. Sample preparation step (601) begins with the user placing saliva on a sample collection means and the system stores the time of saliva sample capture. In the illustrative embodiment the saliva sample is captured by the user on a lateral flow sample strip which may be enhanced with an optional glucose level indicator. Pharmaceutical data capture step (603) is achieved by a patient entering the administration time and dosage information of the pharmaceutical presently administered to the patient. In the illustrative example a smartphone is used which may alternately be a personal computer or dedicated device. The pharmaceutical data capture may be inputted manually by the patient and may alternately be captured automatically by using near field communication (NFC) or alternate means. The sample is sent by mail or otherwise transported to a central analysis facility and analyzed by liquid chromatography and mass spectrometry (LC/MS) during sample chemical analysis step (605) to determine body levels of metformin pharmaceutical. While the illustrative example utilizes a centralized LC/MS analysis platform other foreseen and intended variants may utilize localized dedicated analysis platforms.

The remainder of Example 2 illustrated by FIG. 6 takes place in a computational or cloud computing environment. During data analysis step (607) body levels of the pharmaceutical metformin are analyzed against time of administration and amount of administration together with body glucose levels. Data transmission step (609) transmits the user body metformin level results to the user's preferred computational device including smartphone and smart watch. Data reporting step (611) provides the user with body metformin levels as a function of time. Optional data alert/feedback gathering step (613) reports abnormal or medically dangerous drug levels to the user as well as medical providers and designated family members and provides an opportunity for gathering user feedback. Data mining step (615) provides a deeper analysis into metformin drug administration as a function of time and behavior as greater data is collected by the system.

In a more specific illustrative embodiment, sample preparation step (601) begins with a user taking Metformin placing a saliva sample collection means in the mouth to collect saliva and takes a digital photo of the lateral flow sample strip with a smartphone. The strip may optionally contain glucose sensing means. After exposure to saliva the user takes a photo of the strip which captures the time of strip exposure and provides time and body glucose data to the system. The saliva capture means is associated to the system by way of 2D bar code, machine readable numbers or other identifiable characteristics. Pharmaceutical data capture step (603) takes place with the user inputting pharmaceutical details of metformin dosage and latest time of administration. Input may be through smartphone, smart watch, stand alone computer or other dedicated computing device. After saliva exposure and smartphone photo capture the sample is placed into a prepaid envelope provided during purchase in the consumer packaging and is sent by mail or otherwise transported to a central analysis facility and analyzed by liquid chromatography and mass spectrometry (LC/MS) during sample chemical analysis step (605). Unlike blood or other biological material collection, the sample is safe at room temperature and does not create hazardous waste handling concerns.

FIG. 4 illustrates the potential for mismatch between pharmaceutical administration and optimal drug levels for glucose management. FIG. 5 is representative of the healthier and more beneficial alignment of metformin drug levels. A primary objective of the system of FIG. 6 is to translate the saliva capture metformin data into actionable lifestyle changes to target drug levels for optimal effect. Once the drug levels are determined, data analysis step (607) takes place in a cloud computing environment to analyze body levels of metformin against time of administration and body glucose levels to determine the best time when the drug should be taken for optimal beneficial effect. The results are wirelessly transmitted over the internet during data transmission step (609) and the user's smartphone or smartwatch user interface displays a high level metadata analysis during data reporting step (611). Unlike traditional Physician's Desk Reference (PDR) or pharmaceutical packet insert materials, the data is presented in plain language and can be as simple as "You've been taking your pill at 4:00 PM. Why don't you try it at 8:00 AM and see if you feel better?"

Use of the claimed system is an iterative process, the more times the user provides results the more powerful the data becomes for user lifestyle wellness management. Optional data alert/feedback gathering step (613) is available to alert the user, designated family members and medical providers if critical overdose or dose omission is detected during sample analysis. Feedback can also be obtained as a result of change in behavior and can be as simple as the system asking the user "Now that you are taking your pill at 8:00 AM, do you feel better?" Data mining step (615) provides a deeper analysis into metformin drug administration as a function of time and behavior as greater data is collected by the system. While artificial intelligence cloud computing provides a computationally powerful tool, the smartphone/smart watch user interface report of data aggregation is intended to be simple by design. Aggregate results in this illustrative example are provided in a simple format. The user receives a monthly snapshot of "You took your pill on time twenty-eight days out of thirty this month, great job! Your feedback says your pill works best when you take it at 9:27 AM, glad to see it is working better. You also switched to a generic version on day 15 and reported no adverse effects, based on your cost data this month you saved $317 because of the switch!"

Figure 7:
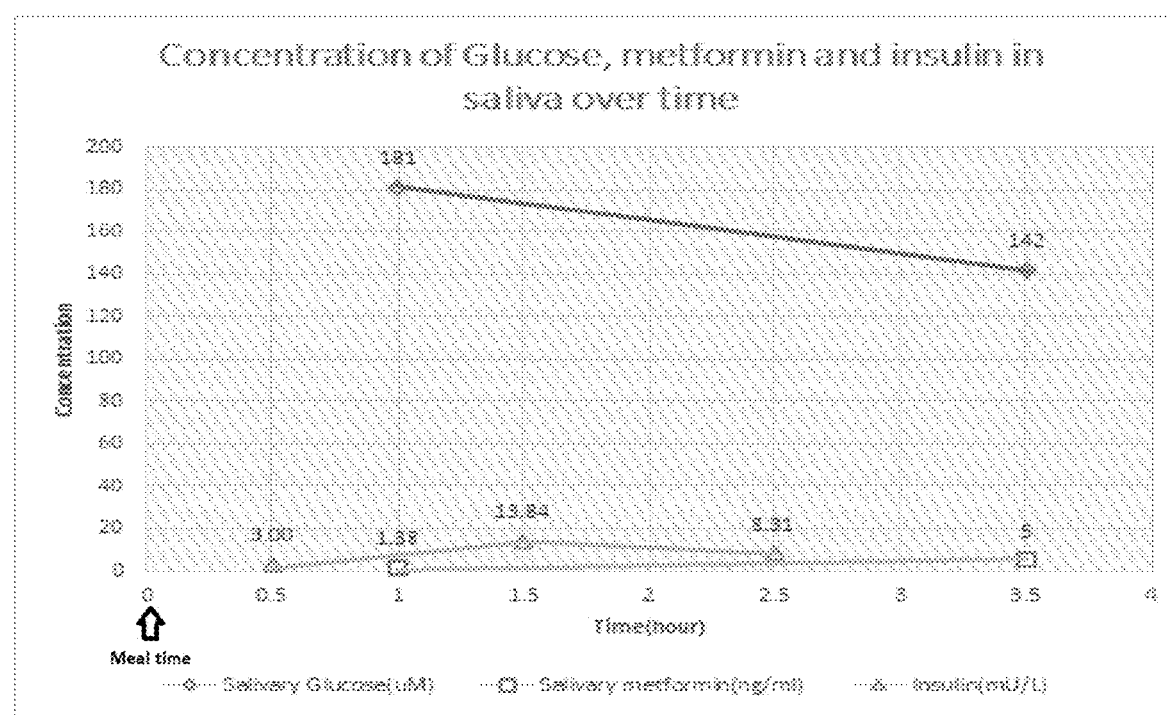
FIG. 7 is a graphical chart illustration of saliva derived metformin, glucose and insulin levels plotted by time.

FIG. 7 reflects an alternate embodiment of the claimed invention where locally obtained glucose results are augmented with subsequent metformin and insulin results determined by LC/MS and ELISA.

Example 3

Figure 8:
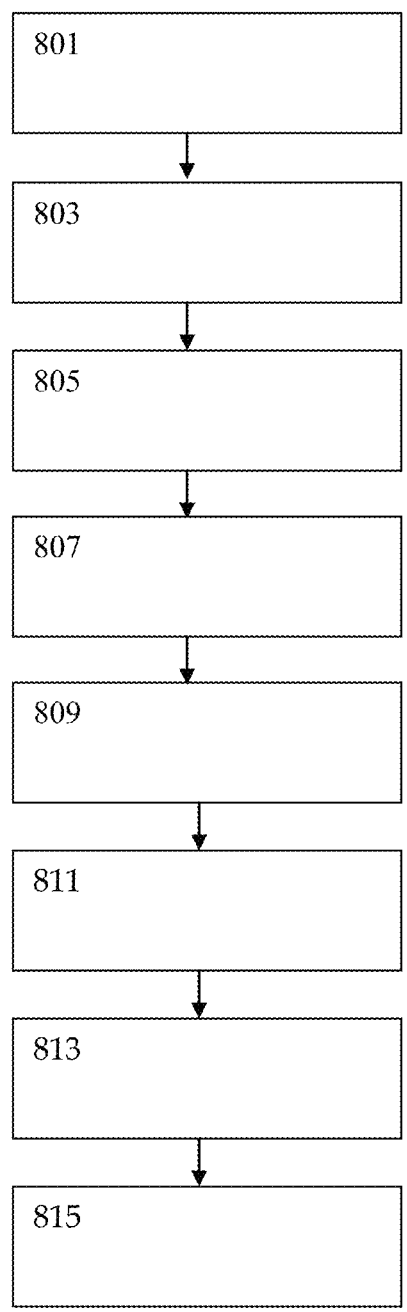
FIG. 8 is a flowchart illustrating a preferred embodiment of the claimed invention.

In a third illustrative example, expanded personalized wellness information is obtained by substitution of an indicator aptamer in place of or augmenting glucose sensing. In addition, LC/MS pharmaceutical detection is supplemented with DNA and RNA sequencing of the saliva sample as well as optional ELISA analysis. In the third illustrative example the presence or absence of the drug Keppra is determined. In FIG. 8, sample preparation step (801) begins with a user in need of medical monitoring placing a saliva sample collection means in the mouth to collect saliva and takes a digital photo of the sample strip with a smartphone. The strip optionally contains one or more aptamers embedded in the saliva collection device which can undergo an optical or machine readable detection upon hybridization. After exposure to saliva the user takes a photo of the lateral flow sample strip which captures the time of strip exposure and provides capture time and optional aptamer data to the system. The saliva capture means is associated to the system by way of 2D bar code, machine readable numbers or other identifiable characteristics. Pharmaceutical data capture step (803) takes place with the user inputting pharmaceutical details of Keppra dosage and latest time of administration. Input may be through smartphone, smart watch, stand alone computer or other dedicated computing device. After saliva exposure and smartphone photo capture the sample is placed into a prepaid envelope provided during purchase in the consumer packaging and is sent by mail or otherwise transported to a central analysis facility and analyzed by liquid chromatography and mass spectrometry (LC/MS) as well as genetic sequencing during sample chemical and genetic analysis step (805). Unlike blood or other biological material collection, the saliva sample is safe at room temperature and does not create hazardous waste handling concerns.

Data analysis step (807) takes place in a cloud computing environment to analyze body levels of pharmaceutical Keppra against time of administration and aptamer and/or genetic sequence indicated and genetic sequencing indicated conditions to determine the best time when the drug should be taken for optimal beneficial effect. In a foreseeable and intended embodiment the presence or absence of pharmaceutical carriers as well as multi-drug detection is carried out by the LC/MS system to determine if the pharmaceutical product is counterfeit and if the user is at risk from multi-drug cross reactions. In an intended alternate embodiment the presence or absence of illicit substances is also detected. Furthermore, the genetic sequencing and data analysis of the saliva sample allows for detection of bacterial and viral infections by screening for miRNA and DNA targets of interest.

The results are wirelessly transmitted over the internet during data transmission step (809) and the user's smartphone or smartwatch user interface displays a high level metadata analysis during data reporting step (811). Unlike traditional Physician's Desk Reference (PDR) or pharmaceutical packet insert materials, the data is presented in plain language and can be as simple as "You've been taking your medication regularly but it looks like you may have a bacterial infection as well. Have you noticed a health change or consulted your physician?"

Use of the claimed system is an iterative process, the more times the user provides results the more powerful the data becomes for user lifestyle wellness management. Optional data alert/feedback gathering step (813) is available to alert the user, designated family members and medical providers if critical overdose, dose omission or counterfeit pharmaceutical product is detected during sample analysis by screening for both pharmaceutical product as well as commonly used pharmaceutical carriers. Feedback can also be obtained as a result of change in behavior and can be as simple as the system asking the user "It looks like you inadvertently took a double dose of your product last week. Now that you are taking your pill at its recommended levels again, do you feel better?" Data mining step (815) provides a deeper analysis into drug administration as a function of time and behavior as greater data is collected by the system. While artificial intelligence cloud computing provides a computationally powerful tool, the smartphone/smart watch user interface report of data aggregation is intended to be simple by design. Aggregate results in this illustrative example are provided in a simple format for improved user personalized health. While illustrative genetic sequence indicators are provided as sequence ID number 1 for H3N2 flu, sequence ID number 2 for H1N1 flu and sequence ID number 3 for e. Coli, the sequences are by way of illustration and not intended to limit the scope or reach of the use of the claimed invention incorporating genetic sequence information.

FIGS. 9 to 14 further illustrate the detection of Keppra in saliva. Levetiracetam (Trade Name: Keppra), is a medication used to treat epilepsy. In the illustrative example, the saliva specimens are collected on 2 separate days. On each day, subject is asked to collect blood/saliva samples before taking Keppra (time=0 hour), and after taking the drug (time=1, 2, 4, 8 hours). Saliva samples are collected in both liquid and dried spot forms. Blood samples are collected in dried spot form and are stored at room temperature before transportation for analytical laboratory analysis using LC/MS.

Figure 9:
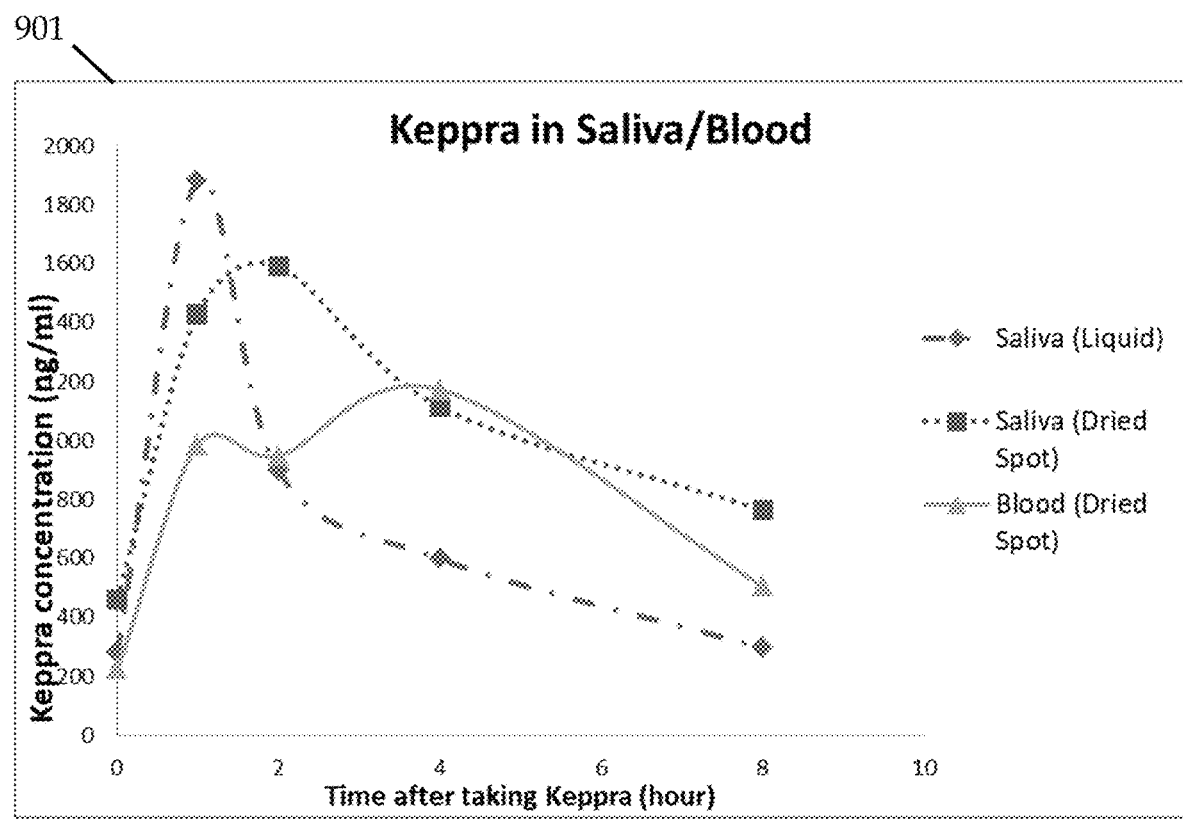
FIG. 9 is a graphical representation of Keppra levels initially measured using saliva and blood.

FIG. 9 is a graphical representation of Keppra levels initially measured using saliva and blood. FIG. 9 graphical illustration 901 comparatively measures alternate saliva sample collection means compared with blood samples.

Figure 10:
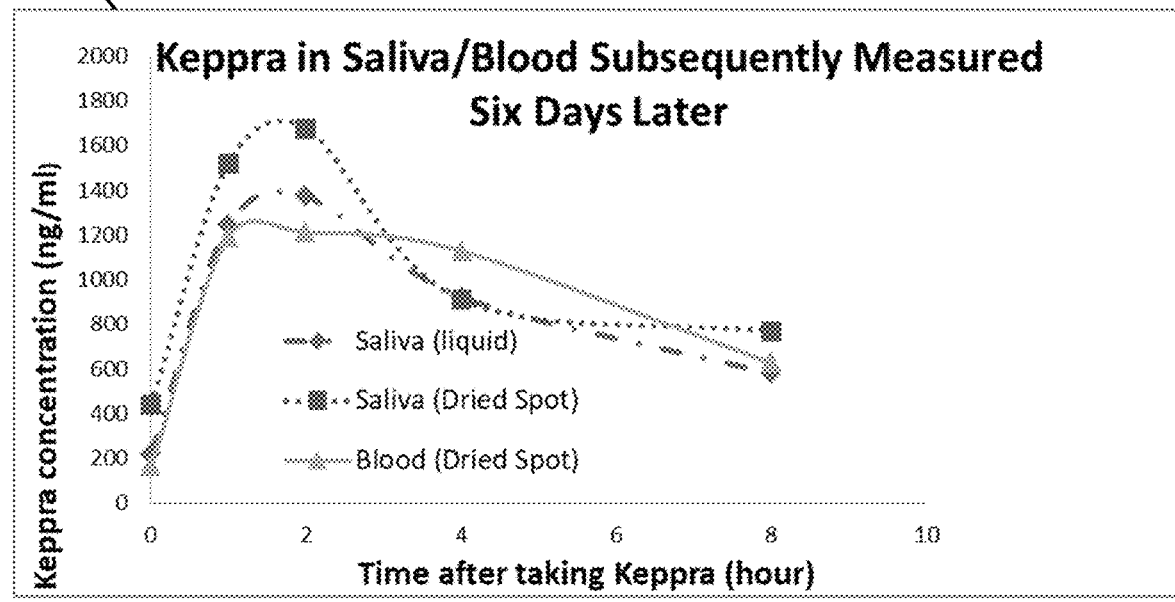
FIG. 10 is a graphical representation of Keppra levels subsequently measured using saliva and blood.

FIG. 10 is a graphical representation of Keppra levels subsequently measured using saliva and blood. FIG. 10 graphical illustration 1001 comparatively measures subsequently measured alternate saliva sample collection means compared with blood samples.

Figure 11:
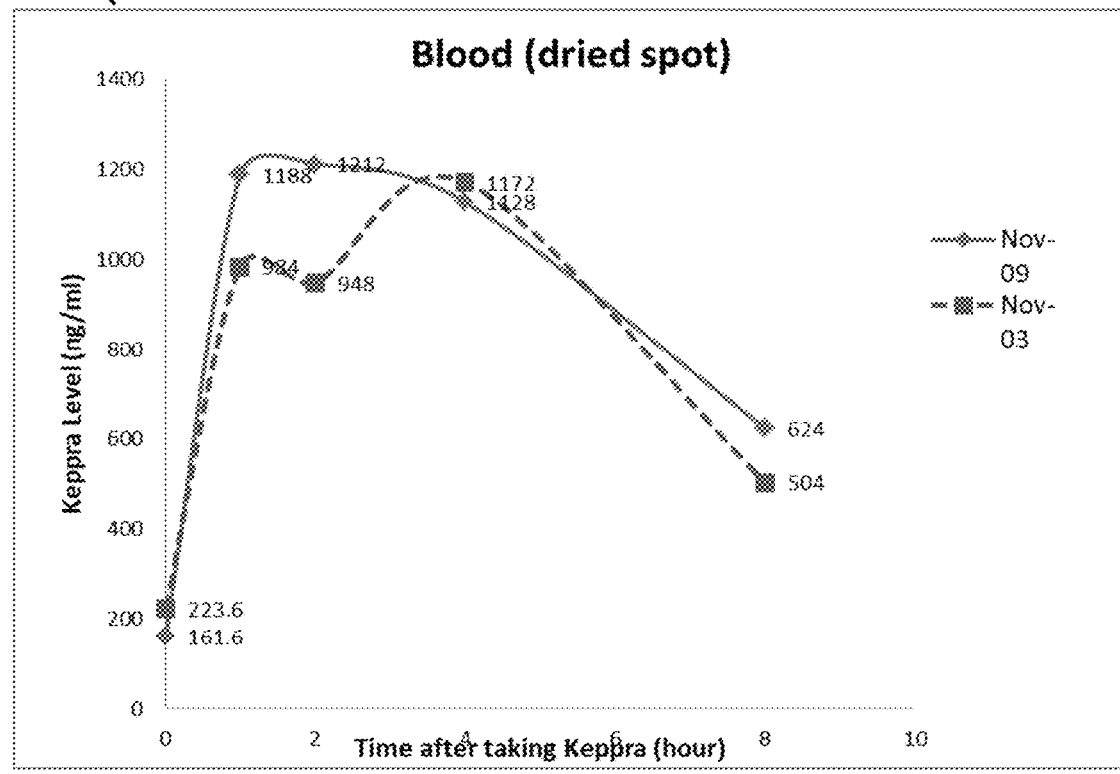
FIG. 11 is a graphical representation of Keppra levels using blood comparatively measured.

FIG. 11 is a graphical representation of Keppra levels using blood comparatively measured. Graphical representation 1101 illustrates the comparison of dried blood spot samples over two separate days.

Figure 12:
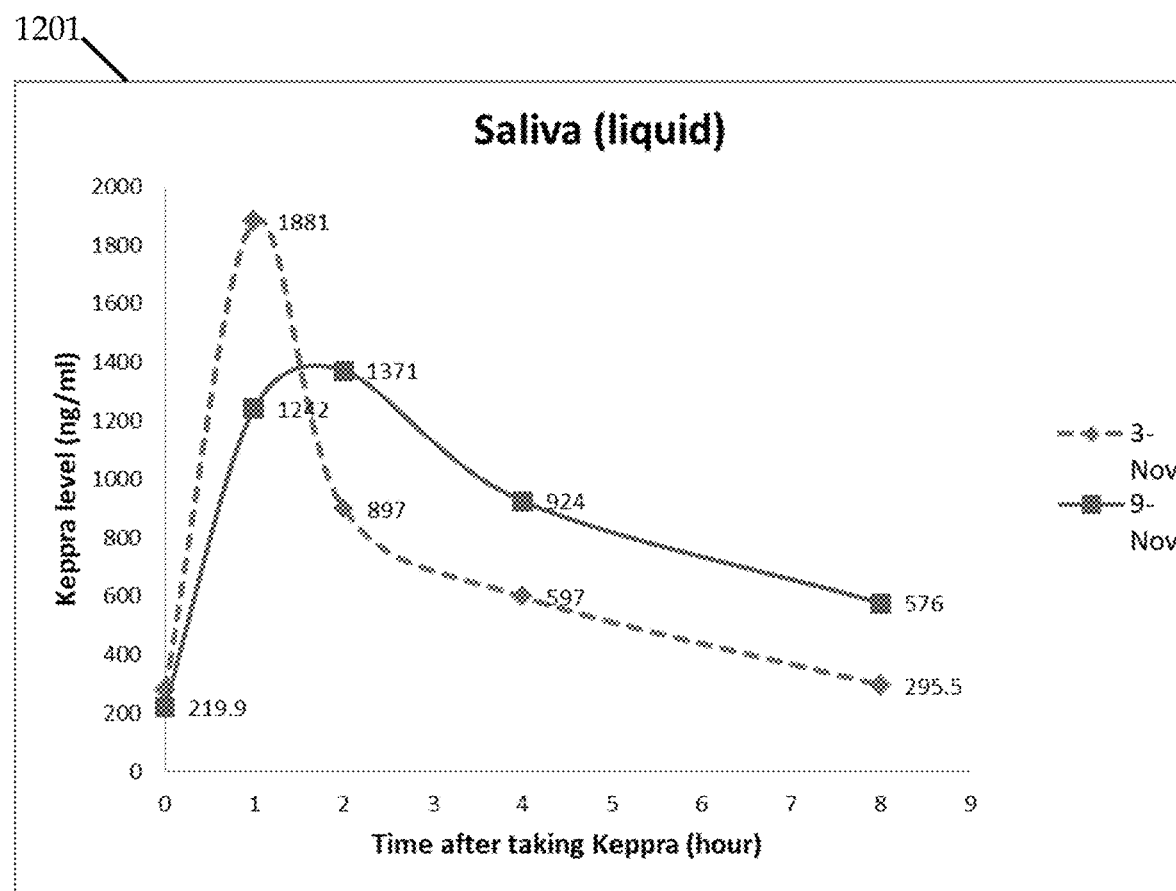
FIG. 12 is a graphical representation of Keppra levels using liquid saliva comparatively measured.

FIG. 12 is a graphical representation of Keppra levels using liquid saliva comparatively measured. Graphical representation 1201 illustrates the comparison of liquid saliva samples over two separate days.

Figure 13:
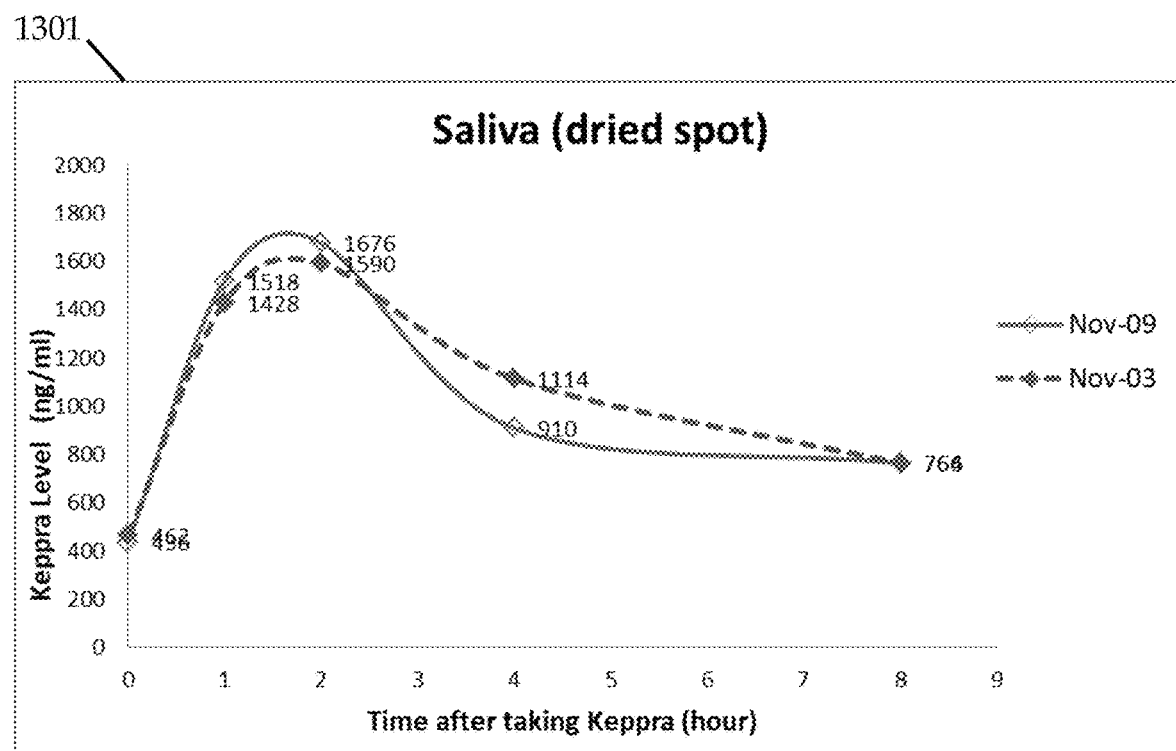
FIG. 13 is a graphical representation of Keppra levels using dried saliva comparatively measured.

FIG. 13 is a graphical representation of Keppra levels using dried saliva comparatively measured. Graphical representation 1301 illustrates the comparison of dried saliva spot samples over two separate days. Dried saliva spot samples from the two days demonstrate the best correlation. Paper-based saliva samples are more stable and consistent compared to blood and liquid saliva samples.

Figure 14:
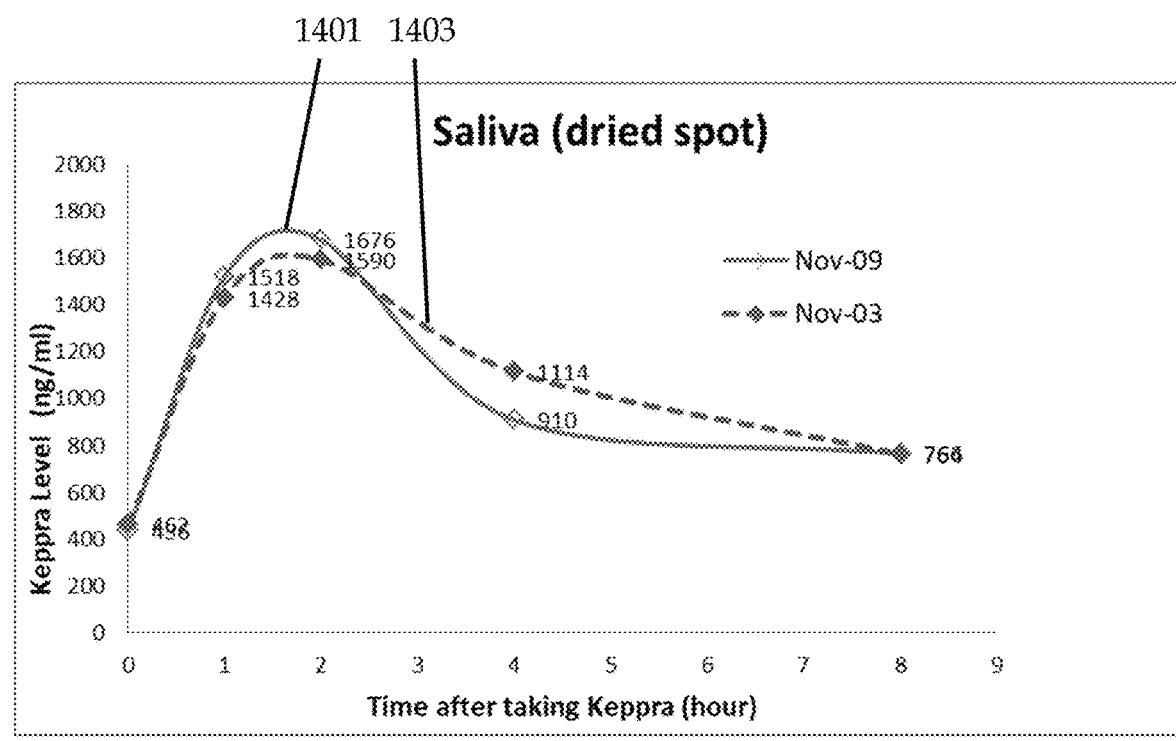
FIG. 14 is a graphical representation of Keppra levels using dried saliva comparatively measured.

FIG. 14 is a graphical representation of Keppra levels using dried saliva comparatively measured. The half-life of Keppra is known to be 5-8 hours. Dried spot saliva samples 1401, 1403 demonstrate that Keppra level depleted by half after 8 hours. Consequently, dried spot saliva samples reliably reflect clearance of Keppra from the body according to the claimed invention.

Figure 15:
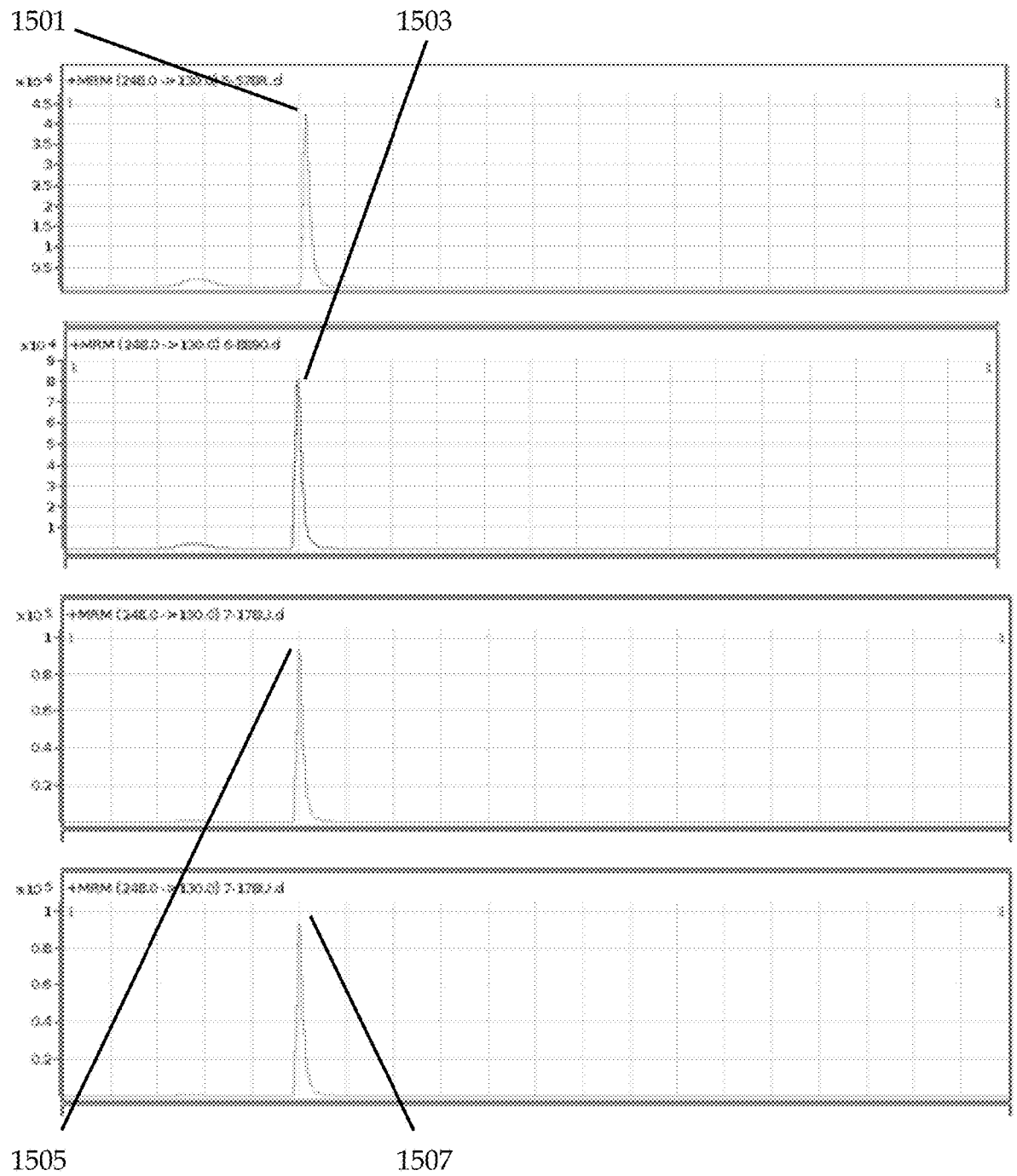
FIG. 15 is a graphical representation of HIV medication FTC levels using saliva.
Figure 16:
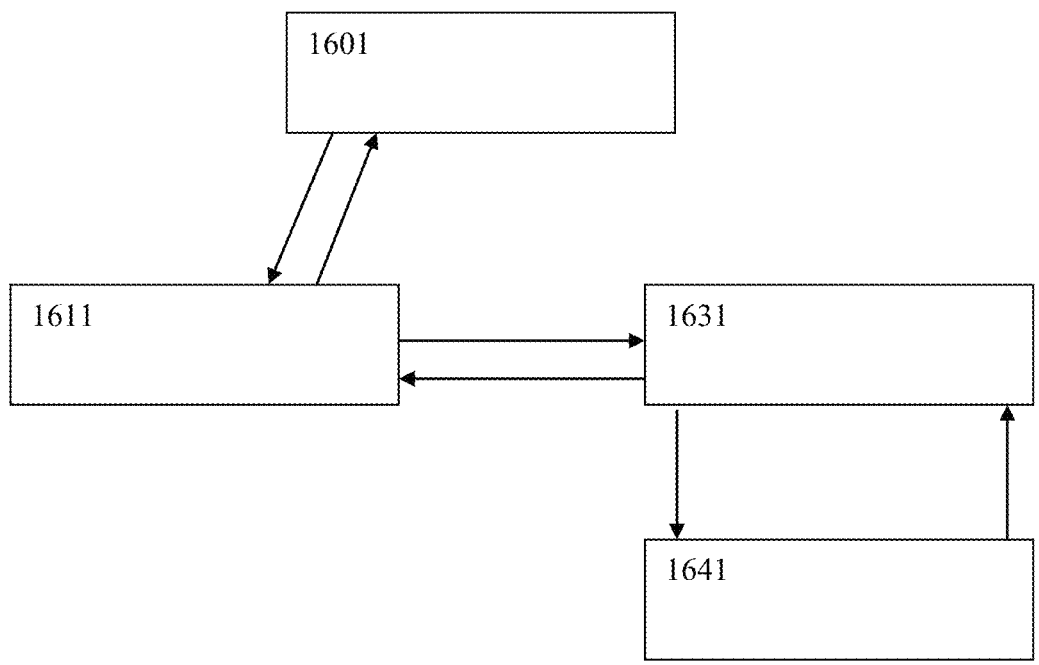
FIG. 16 is a flowchart illustrating a preferred embodiment of the claimed invention.

The system of the third example is illustrated in FIGS. 15 to 18. In a third illustrative example, the detection of a HIV drug in saliva is conducted according to the claimed invention. FTC is a drug component that is found in 80% of HIV medications. FIG. 15 illustrates the detection of the FTC fragment ion (1501, 1503, 1505, 1507) in all subjects via LC/MS. In FIG. 16, results from saliva sample collection device (1641) are captured by personal communication device (1631) incorporating one or more central processing units, one or more cameras and internet connection means. Health sample analysis hardware (1601) further analyzes saliva sample collection device (1641) with results communicated through health sample interpretation software, artificial intelligence element and cloud computing element (1611) for interpretation and communication of saliva sample health care results (not shown). Saliva sample collection device (1641) may optionally contain one or more health sample detection chemicals as well as one or more health sample detection aptamers or DNA/RNA sample detection regions. Sample analysis hardware includes chromatography and mass spectrometry functionality and can additionally include genetic sequencing functionality.

Figure 17:
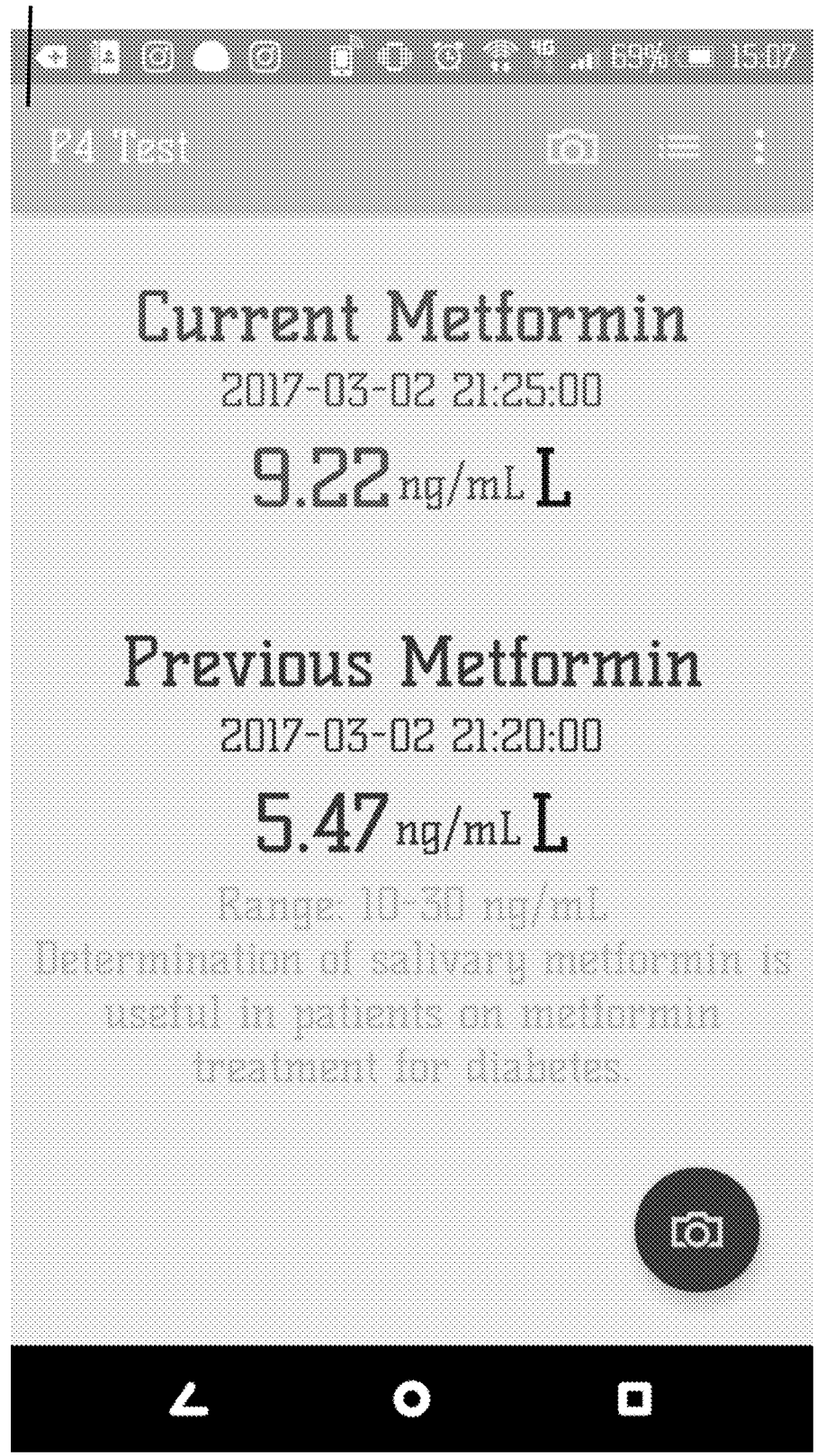
FIG. 17 is a diagram of a screen capture of a preferred embodiment of the claimed invention.

FIG. 17 is a diagram of a screen capture of a preferred embodiment of the claimed invention. In addition to providing real-time salivary glucose levels, P4 precision wellness information additionally incorporates pharmaceutical level results smartphone reported to the user's smartphone screen as illustrated. In the illustrative example current and previous metformin levels (1701) are represented.

Figure 18:
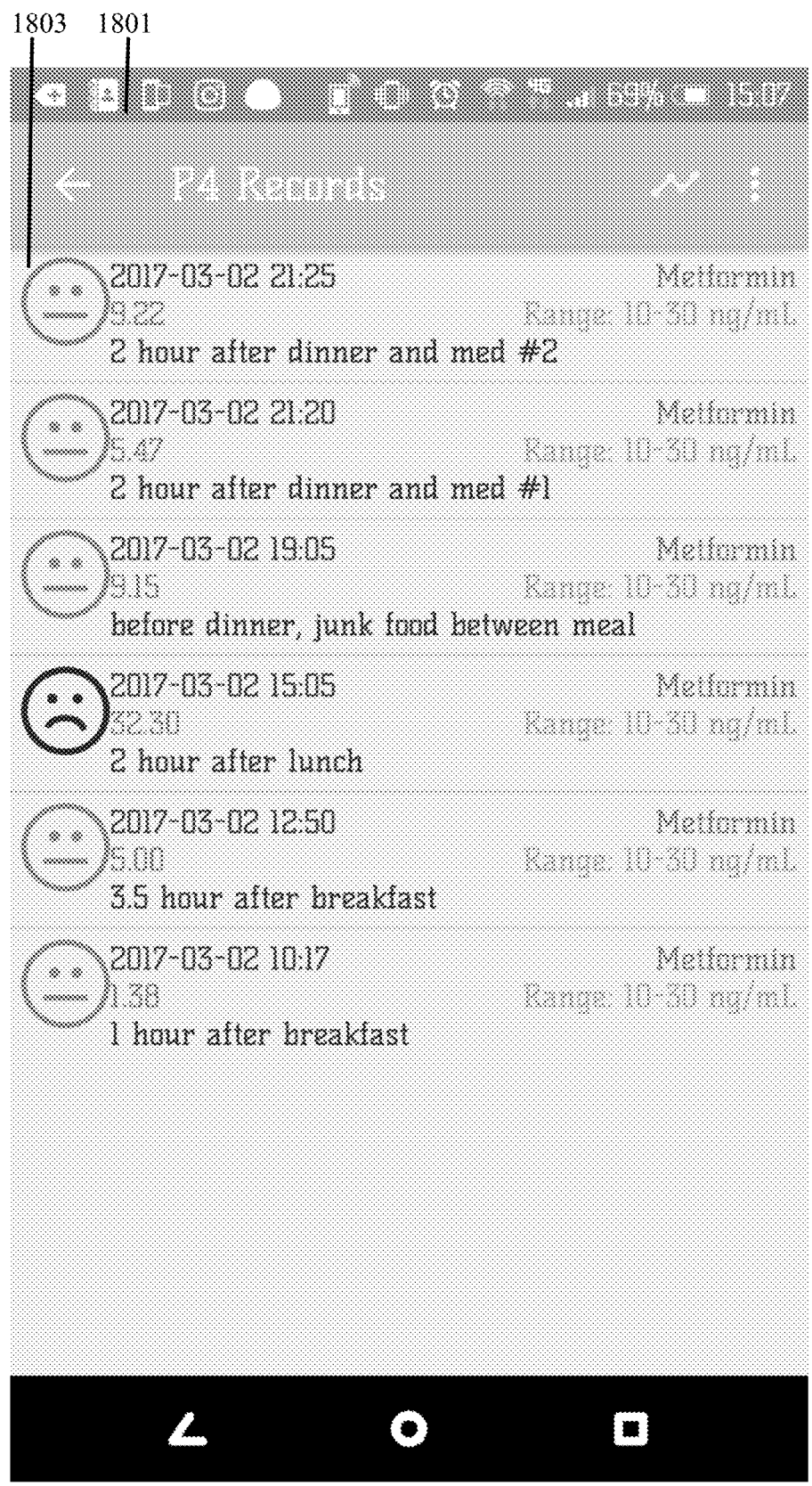
FIG. 18 is a diagram of a screen capture of a preferred embodiment of the claimed invention.

FIG. 18 is a diagram of a screen capture of a preferred embodiment of the claimed invention. Smartphone screen capture (1801) additionally incorporates a wide range of user pharmaceutical administration updates illustrated by easy to understand wellness icon (1803) summaries.

In the description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

INDUSTRIAL APPLICABILITY

The claimed invention has industrial applicability in the biomedical arts. In particular, the claimed invention is directly relevant to the therapeutic administration of pharmaceuticals for mitigation of and therapeutic effects against diseases.

---
Sequence Listing

Name Sequence

---

Seq. ID. No. 1
H3N2
CTCATCTTACCCTTTTTCTCCTCTG

Seq. ID. No. 2
H1N1
TTTACCTCCTCTTTTCGTACTCTCC

Seq. ID. No. 3
E.coli
GGTGGTGGCGGGGGGTGGGGGGGTT

--- hardware, health sample interpretation software, artificial intelligence element and cloud computing element with real-time interpretation and communication of saliva sample health care results wherein said saliva sample collection device additionally comprises one or more health sample detection aptamers and wherein said saliva sample collection device additionally comprises one or more health sample detection aptamers including aptamers having Seq ID #1.

2. The system of claim 1 wherein said health sample subsequent analysis hardware additionally comprises enzyme-linked immunosorbent assay (ELISA) chemical analysis functionality.

3. A personal health monitoring system comprising:

A saliva sample collection device, a smartphone personal communication device incorporating one or more central processing units, one or more cameras, internet connection means, health sample subsequent analysis hardware, health sample interpretation software, artificial intelligence element and cloud computing element with real-time interpretation and communication of saliva sample health care results wherein said saliva sample collection device additionally comprises one or more health sample detection aptamers and wherein

I claim:

1. A personal health monitoring system comprising:
A saliva sample collection device, a smartphone personal communication device incorporating one or more central processing units, one or more cameras, internet connection means, health sample subsequent analysis hardware, health sample interpretation software, artificial intelligence element and cloud computing element with real-time interpretation and communication of saliva sample health care results wherein said saliva sample collection device additionally comprises one or more health sample detection aptamers including aptamers having Seq ID #2.

4. The system of claim 3 wherein said health sample subsequent analysis hardware additionally comprises chromatography and mass spectrometry functionality.

5. A personal health monitoring system comprising:

A saliva sample collection device, a smartphone personal communication device incorporating one or more central processing units, one or more cameras, internet connection means, health sample subsequent analysis hardware, health sample interpretation software, artificial intelligence element and cloud computing element with real-time interpretation and communication of saliva sample health care results wherein said saliva sample collection device additionally comprises one or more health sample detection aptamers and wherein said saliva sample collection device additionally comprises one or more health sample detection aptamers including aptamers having Seq ID #3.

6. The system of claim 5 wherein said health sample analysis subsequent hardware additionally comprises genetic sequencing functionality.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct created by rational design

<400> SEQUENCE: 1
ctcatcttac ccttttctc ctctg                                    25

<210> SEQ ID NO 2
<211> LENGTH: 25
<212> TYPE: DNA
<213> ORGANISM: Artificial Sequence
<220> FEATURE:
<223> OTHER INFORMATION: Synthetic construct created by rational design

<400> SEQUENCE: 2
tttacctcct cttttcgtac tctcc                                   25

<210> SEQ ID NO 3
<211> LENGTH: 25
<212> TYPE: DNA
<213> ORGANISM: Artificial Sequence
<220> FEATURE:
<223> OTHER INFORMATION: Synthetic construct created by rational design

<400> SEQUENCE: 3
ggtggtggcg gggggtgggg gggtt                                   25